United States Patent
El-Naggar et al.

(10) Patent No.: US 7,338,971 B2
(45) Date of Patent: Mar. 4, 2008

(54) TREATMENT OF INFLAMMATORY, CANCER, AND THROMBOSIS DISORDERS

(76) Inventors: Mawaheb M. El-Naggar, 7 Linden Cir., Lincoln Univ., PA (US) 19352; Ahmed S. Mousa, 7 Linden Cir., Lincoln Univ., PA (US) 19352

( * ) Notice: Subject to any disclaimer, the term of this patent is extended or adjusted under 35 U.S.C. 154(b) by 114 days.

(21) Appl. No.: 09/943,048

(22) Filed: Aug. 30, 2001

(65) Prior Publication Data

US 2003/0045562 A1    Mar. 6, 2003

(51) Int. Cl.
*A61K 31/415* (2006.01)
*A61K 31/382* (2006.01)
*A61K 31/198* (2006.01)
*A61K 31/407* (2006.01)
*A61K 31/365* (2006.01)

(52) U.S. Cl. .............. 514/406; 514/432; 514/413; 514/455; 514/161

(58) Field of Classification Search ........... 514/406, 514/432, 413, 456, 570, 568
See application file for complete search history.

(56) References Cited

U.S. PATENT DOCUMENTS

| | | | | |
|---|---|---|---|---|
| 4,501,755 A | * | 2/1985 | Wu | 514/456 |
| 5,196,448 A | * | 3/1993 | Ely | 514/452 |
| 5,399,584 A | * | 3/1995 | Ares et al. | 514/432 |
| 6,248,341 B1 | * | 6/2001 | Anderson et al. | 424/401 |
| 6,267,985 B1 | * | 7/2001 | Chen et al. | 424/451 |
| 6,306,842 B1 | * | 10/2001 | Lai et al. | 514/159 |
| 6,444,221 B1 | * | 9/2002 | Shapiro | 424/451 |
| 6,534,086 B1 | * | 3/2003 | Krumhar | 424/464 |
| 6,541,613 B2 | * | 4/2003 | Hendler et al. | 536/8 |
| 6,552,031 B1 | * | 4/2003 | Burch et al. | 514/282 |
| 6,569,463 B2 | * | 5/2003 | Patel et al. | 424/497 |
| 6,576,271 B2 | * | 6/2003 | Nair et al. | 424/735 |
| 2004/0235802 A1 | * | 11/2004 | Gimona | 514/156 |

FOREIGN PATENT DOCUMENTS

| | | | |
|---|---|---|---|
| DE | 19855426 A1 | * | 6/2000 |
| WO | WO 0145705 A1 | * | 6/2001 |
| WO | WO 0158441 A1 | * | 8/2001 |

OTHER PUBLICATIONS

"Anti-inflammatory and anti-allergic properties of flavonoids", Gabor M., Prog Clin Biol Res 213:471-480, 1986.*
"A New Cyclooxygenase-2 Inhibitor, Rofecoxib (VIOXX), Did Not Alter the Antiplatelet Effects of Low-Dose Aspirin in Healthy Volunteers", Greenberg et al., Journal of Clinical Pharmacology, 2000, 40(12. Pt2), pp. 1509-1515.*
Drug Facts and Comparison, 1995 Edition, pp. 1248.*

* cited by examiner

*Primary Examiner*—Brian Kwon
(74) *Attorney, Agent, or Firm*—Schmeiser, Olsen & Watts

(57) ABSTRACT

This invention provides for the treatment of inflammatory, cancer and thrombotic disorders through the administration, in combination, of a COX2 inhibitor, low dose aspirin, and antioxidant flavanoids, flavonoids or isoflavones and at least one of these combinations will be given in a subtherapeutic amount for improved anti-inflammatory, anti-cancer, and anti-thrombotic efficacy and safety.

8 Claims, No Drawings

TREATMENT OF INFLAMMATORY, CANCER, AND THROMBOSIS DISORDERS

FIELD OF THE INVENTION

This invention relates to the combination of enteric-coated low dose aspirin, antioxidants (falvanoids or flavonoids), and COX2 inhibitors for inflammatory, cancer and thrombosis disorders.

BACKGROUND OF THE INVENTION

One of the most adverse effects of nonsteroidal anti-inflammatory drugs (NSAIDs) is their ulcerogenic activity on the gastrointestinal tract. Flavonoids are shown to possess anti-inflammatory efficacy without the ulcerogenic side effects (Parmar N S, Ghosh M N. In Proceedings of the 6$^{th}$ Hungarian Bioflavonoids Symposium. Farkas L., et al. (Ed.), Elsevier, Amsterdam 513-516, 1981). Examples of those flavanoids and flavonoids are as listed in the recent review (Lin J-K, Tsai S-H, Lin-Shiau S-Y. Drugs of the Future 26: 145-152; 2001). Flavanoids, flavonoids, and isoflavones are shown to be effective inhibitors of angiogenesis, tumor growth and tumor metastasis (Igura K, Ohta T, Kuroda Y, Kaji K. cancer Lett. 171:11-16; 2001; Kimura Y, Okuda H. J Nutr. 131: 1844-1849; 2001; Lin J-K, Tsai S-H, Lin-Shiau S-Y. Drugs of the Future 26: 145-152; 2001). The recent marketing of two selective cyclooxygenase 2 (COX-2) inhibitors climaxes the first phase of an exciting and fast-paced effort to exploit a novel molecular target for nonsteroidal anti-inflammatory drugs (NSAIDs). Much has been written in the lay and scientific press about the potential of COX-2 inhibitors as anti-inflammatory and analgesic agents that lack the gastrointestinal side-effects of traditional NSAIDs. Although research on COX-2 inhibitors has focussed mainly on inflammation and pain, experimental and epidemiological data suggest that COX-2 inhibitors could be used in the treatment or prevention of a broader range of diseases. Recent reports suggested increased thrombogenicity of COX2-specific inhibitors (Catella-Lawson F, Crofford L J, Am J Med 110: p28S-32S; 2001) in high risk patients suggesting the need for an adjunct antiplatelet agent.

Antiplatelet therapy has become a standard treatment of acute and chronic arterial thrombotic diseases. Among current available anti-platelet drugs, aspirin is the drug of choice for secondary prevention of myocardial infarction (Schror K. Antiplatelet drugs. Drugs 50:7-28, 1995). Its antiplatelet activity is mainly due to the irreversible inhibition of the platelet cyclo-oxygenase causing a last-lasting blockade of platelet-dependent thromboxane $A_2$ formation. Since pro-inflammatory stimuli might trigger the extension of thromboembolic disorders and vice versa, the combination of standard dose of COX2 inhibitors (anti-inflammatory) and aspirin (antiplatelet+limited anti-inflammatory) at the 70-85 mg would improve the efficacy and safety of each other. Additionally, COX2 inhibitors similar to the flavanoids exhibited anti-angiogenesis and anti-tumor efficacy. Recent studies demonstrated overexpression of COX-2 in multiple human tumors and pharmacological evidence in animal models, which indicate that COX-2 inhibitors could be used in the prevention or treatment of a broader range of disease (Kalgutkar A S, Zhao Z. Curr Drug Targets. 2(1): 79-106, 2001).

Compared with traditional non-steroidal anti-inflammatory drug agents, use of COX-2 selective inhibitors is associated with decreased incidence of adverse gastric events as a result of minimal inhibition of gastroprotective COX-1, but with equivalent anti-inflammatory benefit through inhibition of COX-2. However, there is evidence to suggest that the 'COX-1=constitutive, COX-2=inflammatory' paradigm is less distinct than originally proposed. Furthermore, selective COX-2 inhibitors may have other consequences as a result of the change in the eicosanoid profile. Thus, despite the relatively safe gastrointestinal profile, vigilant post-marketing surveillance for other adverse effects is required (Penglis P S, James M J, Cleland L G., Intern Med J 2001;31(1):37-41). In that regard, recent clinical reports suggested increased thrombotic events in patients taking COX2 inhibitors suggesting the urgent need for the use of the COX1 inhibitory efficacy of aspirin to improve such serious adverse outcome when using COX2 inhibitors for long term.

The recent marketing of two selective cyclooxygenase-2 (COX-2) inhibitors, celecoxib and rofecoxib is remarkable considering that COX-2 was only discovered eight years ago as a growth factor- and cytokine-inducible gene. Concomitant with these pharmaceutical successes is the advances in our understanding of the molecular and structural basis for selective COX2 inhibition. In addition to the existing inhibitor classes, there are many novel structural classes which have recently emerged due to a better understanding of the active site differences between the two isozymes (Kalgutkar A S, Zhao Z., Curr Drug Targets 2001; 2(1): 79-106). In addition to its role in inflammation, recent studies suggest that COX-2 -derived prostaglandin may play a pivotal part in the maintenance of tumor viability, growth, and metastasis. NSAID epidemiological evidence, studies demonstrating overexpression of COX-2 in multiple human tumors and pharmacological evidence in animal models, which indicate that COX-2 inhibitors could be used for the prevention or treatment of a broader range of disease.

SUMMARY OF THE INVENTION

One object of the present invention is to provide a method of preventing thrombotic complications due the long-term use of COX2 inhibitors and to enhance its anti-inflammatory and anticancer efficacy by combining it with low dose enteric coated aspirin and flavanoids. This combination therapy in a mammal comprising: administering to said mammal the combination in a therapeutically effective amount of (i) a COX2 inhibitors selected from the group consisting of celecoxib (Celebrex$^R$), rofecoxib (Vioxx$^R$), and other specific COX2 inhibitors (ii) aspirin and (iii) antioxidants selected from the group consisting of flavanoids, flavonoids or isoflavones, wherein at least one of the COX2 inhibitors, at least one of the flavanoids and aspirin are used.

Another object of the present invention is to provide a method of treating inflammatory disorders, cancer and thrombosis in a mammal wherein the combination of (i) and (ii) or (iii) above are administered in amounts to provide a synergistic effect in improving the efficacy and safety.

DETAILED DESCRIPTION OF THE INVENTION

The combinations of a COX2 inhibitors with aspirin and antioxidants useful in the treatment of inflammatory and thrombotic disorders including rheumatoid arthritis, atherosclerotic arterial disease, valvular heart disease, cerebrovascular disease such as stroke, atrial fibrillation, coronary artery disease such as myocardial infarction and unstable angina, coronary artery bypass grafts, peripheral vascular disease, thromboembolic complications of prosthetic cardiovascular devices such heart valves and vascular grafts. These combinations are also expected to be useful in combining with endovascular stenting procedures such as percutaneous transluminal coronary angioplasty, to prevent subsequent arterial thrombus formation and reocclusion. Also useful in the treatment of thrombosis is the combination in a therapeutically effective amount of tissue plasminogen activator and the GPIIb/IIIa antagonists. Specific examples of useful GPIIb/IIIa antagonist compounds are abciximab, eptifibatide, tirofiban, lamifiban, lefradafiban, sibrafiban (Ro-48-3657), orbofiban and xemilofiban described in the paper of Graul et al. and Scarborough (Graul A, Martel A M and Castaner J. Xemilifiban; Drugs of the Future 22: 508-517, 1997; Scarborough R M; Eptifibatide. Drugs of the Future 23: 585-590, 1998). Of these, lamifiban, lefradafiban, sibrafiban, orbofiban and xemilofiban are preferred. Others will be readily apparent to those skilled in the art.

"Therapeutically effective amount" is intended to include an amount of a combination of compounds claimed effective to treat inflammatory and thrombotic disorders in a mammal.

By "administered in combination", "combination", or "combined" when referring to compounds described herein, it is meant that the compounds or components are administered concurrently to the mammal being treated. When administered in combination each compound or component or component may be administered at the same time or sequentially in any order or at different points in time, so as to provide the desired therapeutic effect.

DOSAGE AND FORMULATION

Combinations of standard doses of COX2 inhibitors, aspirin at doses ranging from 70-350 mg, and antioxidants are administered as treatment for inflammatory, cancer, and thrombotic disorders. They can be administered by any conventional means available for use in conjunction with pharmaceuticals, either as individual therapeutic agents or in a combination of therapeutic agents.

Dosage forms of compositions suitable for administration contain from about 1 mg to about 100 mg of active ingredient per unit. In these pharmaceutical compositions the active ingredient will ordinarily be present in an amount of about 0.5-95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose. starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in Remington's Pharmaceutical Sciences, 17th ed., Mack Publishing Company, Easton, Pa., 1985, a standard reference text in this field, the contents of which are incorporated herein by reference.

Useful pharmaceutical dosage-forms for administration of the compounds of this invention can be illustrated as follows:

Capsules

A large number of unit capsules can be prepared by filling standard two-piece hard gelatin capsules each with 0.1 to 100 mg of powdered active ingredient, 150 mg of lactose, 50 mg of cellulose, and 6 mg magnesium stearic.

Soft Gelatin Capsules

A mixture of active ingredient in digestible oil such as soybean oil, cottonseed oil or olive oil can be prepared and injected by means of a positive displacement pump into gelatin to form soft gelatin capsules containing 0.1 to 100 mg of the active ingredient. The capsules should then be washed and dried.

Tablets

A large number of tablets can be prepared by conventional procedures so that the dosage unit is 0.1 to 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 ml contain 0.1 to 100 mg of finely divided active ingredient, 200 mg of sodium carboxymethyl cellulose, 5 mg of sodium benzoate, 1.0 g of sorbitol solution, U.S.P., and 0.025 mg of vanillin.

The combined compounds of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for combined compounds wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of combined compounds in which the one compound is coated with a sustained and/or enteric release polymer, and the other compound is also coated with a polymer such as a low viscosity grade of hydroxypropyl methylcellulose or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric-coated compound and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the combined compounds, whether administered in a single dosage form or administered in separate forms but at the same time or concurrently by the same manner, will be readily apparent to those skilled in the art, based on the present disclosure.

Combination

Each therapeutic compound of this invention can independently be in any dosage form, such as those described above, and can also be administered in various ways, as described above. For example, the compounds may be formulated together, in a single dosage unit (that is, combined together in one capsule, tablet, powder, or liquid, etc.) as a combination product. Alternatively, when not formulated together in a single dosage unit, an individual COX2 inhibitors may be administered at the same time as either aspirin or antioxidants (flavanoids, flavonoids or isoflavones) or sequentially, in any order thereof.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of a COX2 inhibitor and low dose aspirin (35-150 mg) combination in an enteric coated formulation is the preferred form. By way of general guidance, typically a daily dosage may be about 0.01 milligram to about 1 gram of each component. By way of general guidance, when the compounds are administered in combination, the dosage amount of each component may be reduced by about 70-80% relative to the usual dosage of the component when it is administered alone as a single agent for the treatment of thrombosis, in view of the synergistic effect of the combination.

Obviously, numerous modifications and variations of the present invention are possible in light of the above teachings. It is therefore to be understood that within the scope of the appended claims, the invention may be practiced otherwise than as specifically described herein.

What is claimed is:

1. A method of treating inflammation in a mammal, said method consisting essentially of concurrently administering to said mammal a therapeutic composition, said therapeutic composition comprising: (i) a standard therapeutic dose of a COX2 inhibitor selected from the group consisting of celecoxib and rofecoxib; (ii) low dose aspirin in an amount of 70-85 mg; and (iii) an antioxidant selected from the group consisting of a flavanoid, a flavonoid, an isoflavone, and combinations thereof.

2. The method of claim 1, wherein the antioxidant is the flavanoid.

3. The method of claim 1, wherein the antioxidant is the flavonoid.

4. The method of claim 1, wherein the antioxidant is the isoflavone.

5. A pharmaceutical composition, comprising a therapeutic composition for treating inflammatory disorders in a mammal, said therapeutic composition comprising: (i) a standard therapeutic dose of a COX2 inhibitor selected from the group consisting of celecoxib and rofecoxib; (ii) low dose aspirin in an amount of 70-85 mg; and (iii) an antioxidant selected from the group consisting of a flavanoid, a flavonoid, an isoflavone, and combinations thereof.

6. The pharmaceutical composition of claim 5, wherein the antioxidant is the flavanoid.

7. The pharmaceutical composition of claim 5, wherein the antioxidant is the flavonoid.

8. The pharmaceutical composition of claim 5, wherein the antioxidant is the isoflavone.

* * * * *

UNITED STATES PATENT AND TRADEMARK OFFICE
CERTIFICATE OF CORRECTION

PATENT NO. : 7,338,971 B2
APPLICATION NO. : 09/943048
DATED : March 4, 2008
INVENTOR(S) : EL-Naggar et al.

Page 1 of 1

It is certified that error appears in the above-identified patent and that said Letters Patent is hereby corrected as shown below:

Column 6
Line 36, delete "inflammatory disorders" and insert --inflammation--
Line 37, delete "comprising" and insert --consisting essentially of--

Signed and Sealed this

Twenty-fourth Day of June, 2008

JON W. DUDAS
*Director of the United States Patent and Trademark Office*